United States Patent [19]

Rumberger

[11] Patent Number: 4,467,637
[45] Date of Patent: Aug. 28, 1984

[54] DEBRIS DETECTION SYSTEM AND METHOD

[75] Inventor: William E. Rumberger, Newtown Square, Pa.

[73] Assignee: The Boeing Company, Seattle, Wash.

[21] Appl. No.: 453,978

[22] Filed: Dec. 28, 1982

[51] Int. Cl.³ .............................................. G01N 15/06
[52] U.S. Cl. .................... 73/61 R; 324/204; 340/631
[58] Field of Search ................. 73/61 R; 324/204; 340/631

[56] References Cited

U.S. PATENT DOCUMENTS

| | | | |
|---|---|---|---|
| 3,373,352 | 3/1968 | Huigens | 73/61 R X |
| 3,432,750 | 3/1969 | Botstiber | 324/204 |
| 3,457,504 | 7/1969 | Arthur et al. | 73/61 R X |
| 3,553,672 | 1/1971 | Smith | 340/631 X |
| 3,686,926 | 8/1972 | Miller et al. | 73/61 R |
| 3,748,576 | 7/1973 | Sigournay | 340/631 X |
| 3,878,103 | 4/1975 | Miller et al. | 340/631 X |
| 4,070,660 | 1/1978 | Tauber | 340/631 |
| 4,205,904 | 6/1980 | Skubich et al. | 340/631 |
| 4,219,805 | 8/1980 | Magee et al. | 324/204 X |
| 4,323,843 | 4/1982 | Batham | 324/204 |

FOREIGN PATENT DOCUMENTS 2029580 3/1980 United Kingdom ................ 324/204

Primary Examiner—Gerald Goldberg
Assistant Examiner—Joseph W. Roskos
Attorney, Agent, or Firm—Jones, Tullar & Cooper

[57] ABSTRACT

A debris detection system for detecting debris in a fluid flow in which both a primary and a secondary fluid flow from a fluid reservoir are maintained. The fluid reservoir is situated downstream of the system being served and receives the debris from the system being served. Within the reservoir the primary fluid flow is shielded from all but the colloidal debris received. All non-colloidal as well as colloidal debris is diverted to the secondary fluid flow where the amount and rate of debris accumulation is detected.

23 Claims, 5 Drawing Figures

DEBRIS DETECTION SYSTEM AND METHOD

BACKGROUND OF THE INVENTION

1. Field of the Invention

This invention relates to a system for detecting debris in a fluid flow and in particular to a system in which detection is achieved without disrupting the fluid flow.

2. Prior Art

A popular means of determining incipient deterioration of a mechanical system is to monitor the fluid flow serving the mechanical system, and more specifically to monitor the quantity of debris in the fluid flow. Consider, for example, U.S. Pat. Nos. 3,686,926, 3,878,103 and 4,070,660. The systems described in these patents are all located in the primary fluid flow path. See, for example, FIG. 6 of U.S. Pat. Nos. 3,686,926 and 3,878,103. In the circuit shown, the two screens and the filter are arranged in series in the oil line serving the transmission.

Any detection system which is placed in the primary fluid flow path introduces an added risk, namely, a detection system failure wholly apart from the mechanical system being served. Such a failure will disrupt the fluid flow to the mechanical system, and the consequences of such a disruption could be quite serious. For example, if in a transmission, and in particular the transmission of a helicopter, the detection system failed and lubricating fluid flow to the transmission were disrupted, the transmission could quickly seize, resulting in loss of the helicopter.

OBJECTS AND SUMMARY OF THE INVENTION

An object of this invention, therefore, is to provide the existing state-of-the-debris detection system art with a detection system which separates the detection function from the primary lubrication function, and is therefore safer for the system served.

Another object of this invention is to provide the existing state-of-the-debris detection system art with a detection system according to the previously stated object which permits optimization of debris monitoring without jeopardizing primary lubrication flow.

Another object of this invention is to provide the existing state-of-the-debris detection system art with a detection system including a rate of debris accumulation capability without jeopardizing primary lubrication flow.

Another object of this invention is to provide the existing state-of-the-debris detection system art with a full flow monitoring detection system having the characteristics of the previously stated objects.

Another object of this invention is to provide the existing state-of-the-debris detection system art with a detection system having the characteristics of the previously stated objects and in addition is easily inspectable without disruption to the primary fluid flow system.

Another object of this invention is to provide the existing state-of-the-debris detection system art with a detection system having the characteristics of the previously stated objects and in addition has size discrimination capability.

Another object of this invention is to provide the existing state-of-the-debris detection system art with a method of debris detection in a fluid stream without disrupting flow.

Another object of this invention is to provide the existing state-of-the-debris detection system art with a method of debris detection in a fluid stream having a primary and secondary flow in which a significant warning is rendered as a function of monitoring the debris accumulation in the secondary flow.

According to the invention a secondary fluid flow is introduced into the circuit including the primary fluid flow and a fluid reservoir. The fluid reservoir is situated downstream of the system being served (transmission, for example) and serves as a fluid source for both fluid flows. Upstream of or within the reservoir the primary fluid flow is shielded from all but colloidal debris generated in the system being served and the debris is diverted to the secondary fluid flow. Within the secondary fluid flow there is situated a pump and detecting apparatus located downstream of the pump for indicating amount of debris accumulation. The detecting apparatus in the secondary fluid flow also serves to provide verification for the presence of metallic debris.

Implementation of the invention into the lubricating system of a system being served, such as a transmission, effects an added degree of safety to the system being served because the development of a failure in the system being served can be detected more reliably.

BRIEF DESCRIPTION OF THE DRAWINGS

Five figures have been selected to more fully explain the invention to the person skilled in the art. These relate to a lubrication system for a transmission of a helicopter, and are.

DETAILED DESCRIPTION

A debris detection system for use with a transmission, and in particular a helicopter transmission will be described in greater detail. The invention, however, has application in any fluid flow system subject to debris accumulation.

The lubricating systems of many helicopter transmissions are now dual systems, i.e., they include a primary flow of lubricant and a secondary or auxilliary flow of lubricant. The second or auxilliary flow of lubricant is a lower capacity flow and is required only in the event of failure of the primary flow. This invention utilizes the dual system in a unique manner, in that the secondary flow serves an additional function, i.e., debris detection. If a failure occurs in the primary flow the secondary flow will be available for lubrication. In addition, the secondary flow serves to detect the amount and rate of debris accumulating in the whole lubricating system.

Figure 1:
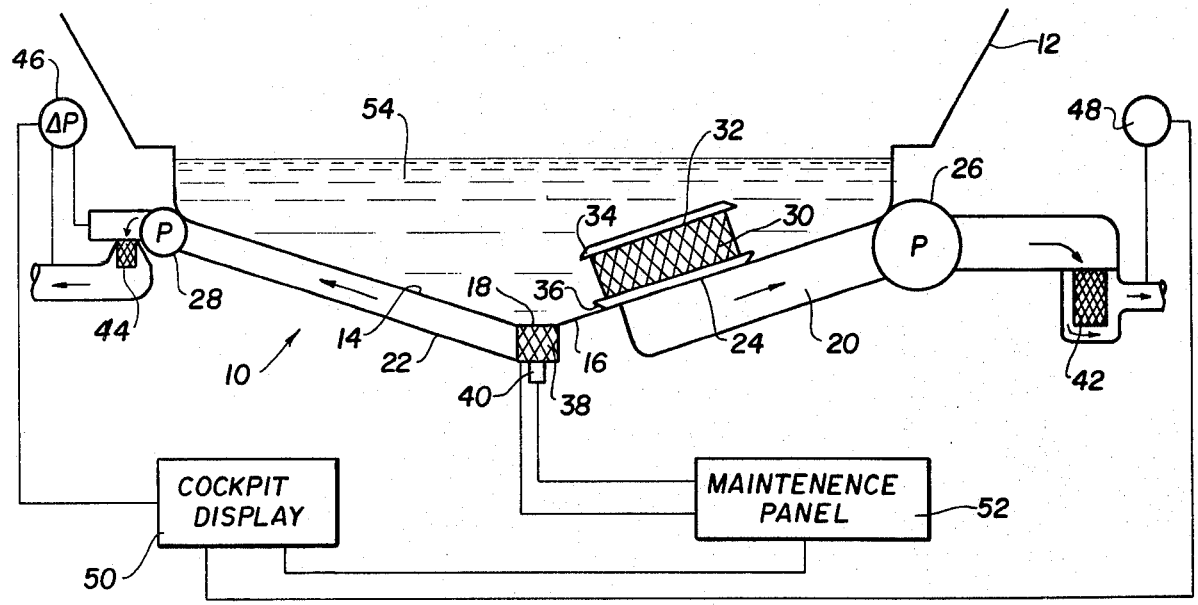
FIG. 1 which schematically illustrates a fluid reservoir with primary and secondary fluid flow-lines and debris detection apparatus in accordance with one embodiment of the invention.
Figure 2:
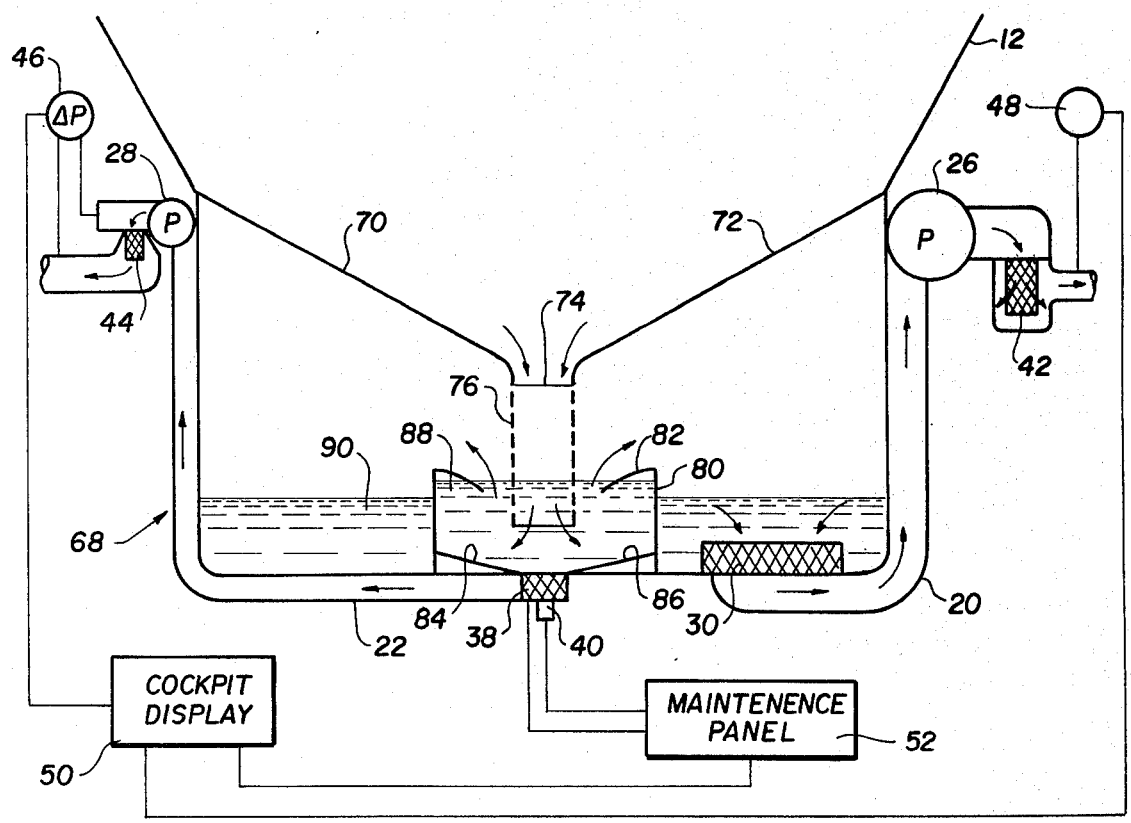
FIG. 2 which schematically illustrates a fluid reservoir with primary and secondary fluid flow lines and debris detection apparatus in accordance with a second embodiment of the invention.
Figure 3:
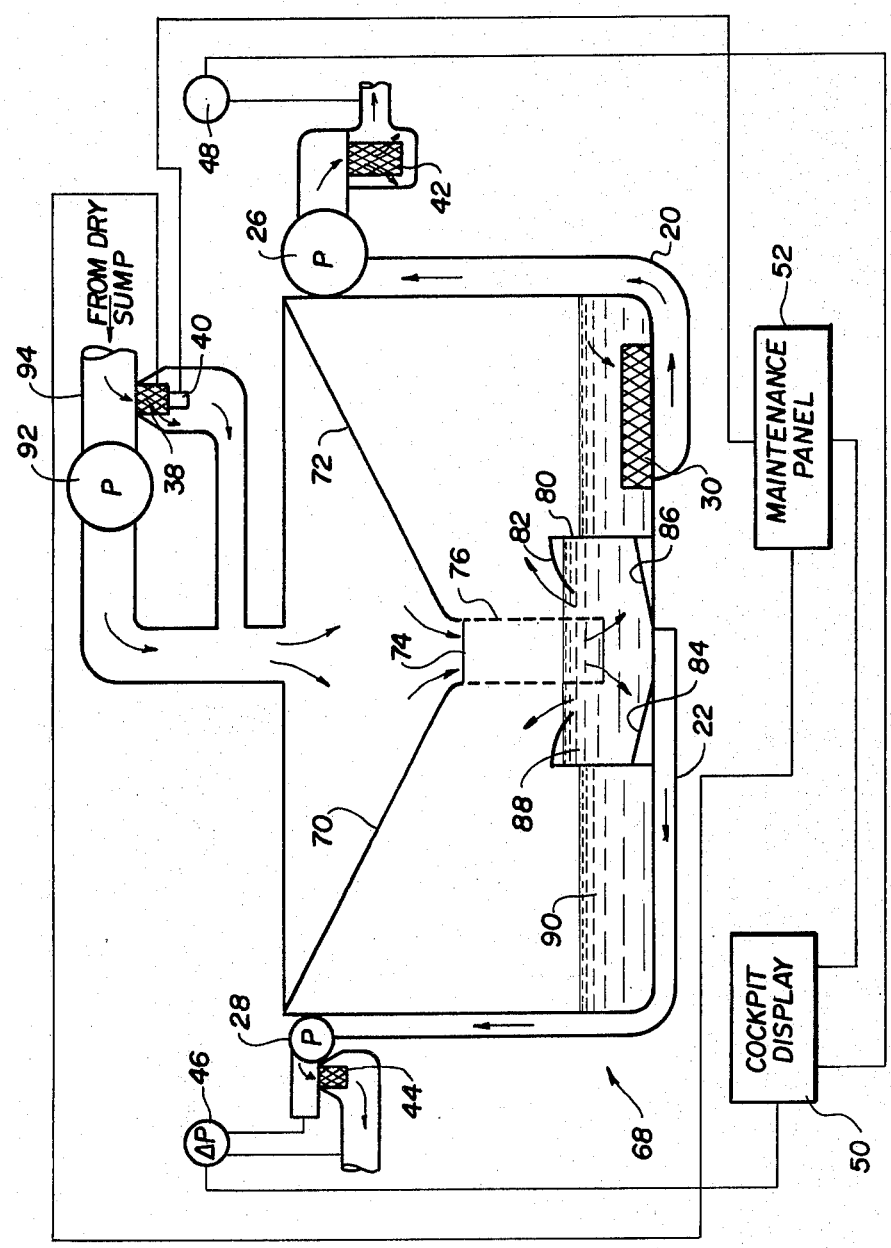
FIG. 3 which schematically illustrates a variant of the second embodiment of FIG. 2.

Structurally, the invention is located at and utilizes the lubricating system reservoir. The reservoir may be a "wet sump", i.e., the reservoir is connected directly to the transmission housing, or a "dry sump", i.e., the reservoir is removed from the transmission housing. FIGS. 1 and 2 illustrate the debris detection system used with a "wet sump", while FIG. 3 illustrates the debris detection system used with a "dry sump".

The reservoir 10 shown in FIG. 1 is mounted directly to the bottom of the transmission 12 (not shown in further detail). The reservoir 10 includes a bottom wall with downwardly tapered sides 14 and 16. The tapered sides 14 and 16 can be representative of only a portion of the bottom wall. Alternatively, the entire wall can be shaped as a cone with the sides 14 and 16 serving as side walls of the cone. In either case the sides 14 and 16 taper downwardly toward each other and meet at an opening 18. Connected to the reservoir 10 is a primary flow line 20 and a secondary or auxilliary flow line 22. An opening 24 in the bottom wall of the reservoir serves as the point of origin for the primary flow through the primary line 20. The opening 18 serves as the point of origin for the secondary flow through the secondary line 22. Each line has its own pump for generating flow such as the pump 26 in the primary line and the pump 28 in the secondary line. The capacity of the primary line is greater than the capacity of the secondary line since the secondary line is intended to serve only as a backup in the event of an emergency. For example, in one helicopter model manufactured by the assignee company the primary flow quantity is approximately 30 gallons per minute while the secondary flow quantity is only approximately 1.5 gallons per minute.

At the opening 24 to the primary flow line 20 a coarse mesh screen 30 is situated. The screen 30 is provided with a cap 32 having a flanged side 34 and a skirt 36. The cap 32 and skirt 36 can be sheet metal plates. They should not be perforated. Downstream of the opening 18 in the secondary line 22 there is located a coarse screen 38 and a magnetic chip detector 40. Preferably, the screen 38 and magnetic chip detector 40 are assembled as a single unit with the magnetic plug situated at the bottom of the screen (when viewed in the direction of flow).

Downstream of the pump 26 in the primary line 20 there is situated a large capacity fine mesh filter 42, while downstream of the pump 28 in the secondary line 22 there is situated a fine mesh screen filter 44. A differential pressure gauge 46 ($\Delta P$) monitors the pressure drop across the filter 44. A pressure gauge 48 is located downstream of the filter 42 and indicates the pressure in the primary flow downstream of the filter 42.

The differential pressure gauge 46 and the pressure gauge 48 are connected to a cockpit display panel 50, while the filter 38 and magnetic chip detector 40 are connected to a maintenance panel 52 which is located at a point in the helicopter remote from the cockpit. The cockpit display 50 and maintenance panel 52 are connected together so that a significant warning can be rendered. This point will be better understood in conjunction with the discussion of FIG. 4.

As previously noted, the reservoir 10 is connected directly to the transmission housing 12 and the oil in the transmission is fed by gravity to the reservoir 10 where the oil forms a pool 54. The pumps 26 and 28 draw the lubricating fluid from the pool 54 through the openings 24 and 18, respectively. As a result, one can envision two streams being created in the pool 54, one flowing toward the opening 24. These streams carry with them some of the debris generated in the transmission itself, i.e., debris in suspension or colloidal debris. This type of debris tends to be very fine having an average size of 0.00001 to 0.000001 inches. It is generated mostly by wear, for example, in the gears and bearings. Another type of debris is not retained in suspension because of its size and consequent weight, and simply falls to the surfaces 14 and 16. This type of debris can also be due to wear, but it can, and frequently is, due to the early stages of failure in, for example, the bearings or gears. When this latter debris reaches the surfaces 14 and 16, it falls, by gravity and the sloping orientation of the surfaces, toward the opening 18.

Only colloidal debris passes the screen 30 as it is shielded from the other debris by the cap 32 and skirt 36. The cap 32 is provided with a flange(s) 34 sloped downwardly and outwardly relative to the screen 30. The skirt 36 has a similar flange(s) sloped upwardly and outwardly relative to the screen 30. The colloidal debris which does pass through the screen 30 is not sufficiently large to damage the pump 26 and is filtered out by the filter 42. The screen 30 therefore serves the primary function of protecting the pump 26 from the large debris particles.

The debris, both colloidal and otherwise, is collected at the opening 18 and for the most part, simultaneously encounters the coarse screen 38 and magnetic chip detector 40. The screen 38 can be constructed similar to that disclosed in U.S. Pat. No. 3,686,926, while the magnetic chip detector 40 can be constructed similar to that disclosed in U.S. Pat. No. 4,070,660. Physically, they can be assembled as a unit, as noted above. If the colloidal debris is of a ferrous nature it will be magnetically attracted to the magnetic chip detector 40. Ferrous debris which is larger than colloidal debris will be magnetically attracted to the magnetic chip detector. When a sufficient quantity of this debris is deposited on detector 40, an indication is relayed to panel 52. The larger particles of debris, i.e., those of sufficient size relative to the mesh size of the screen 38, that is metallic in nature, will impinge on the screen 38 and an indication will be relayed to panel 52. Debris of any kind which passes through opening 18 past the magnetic chip detector 40 and through screen 38 will be collected by the fine screen filter 44. When a sufficient quantity of this debris is collected a pressure change occurs across the filter and the gauge 46 will provide a reading at the panel 50 for pilot observation.

Figure 4:
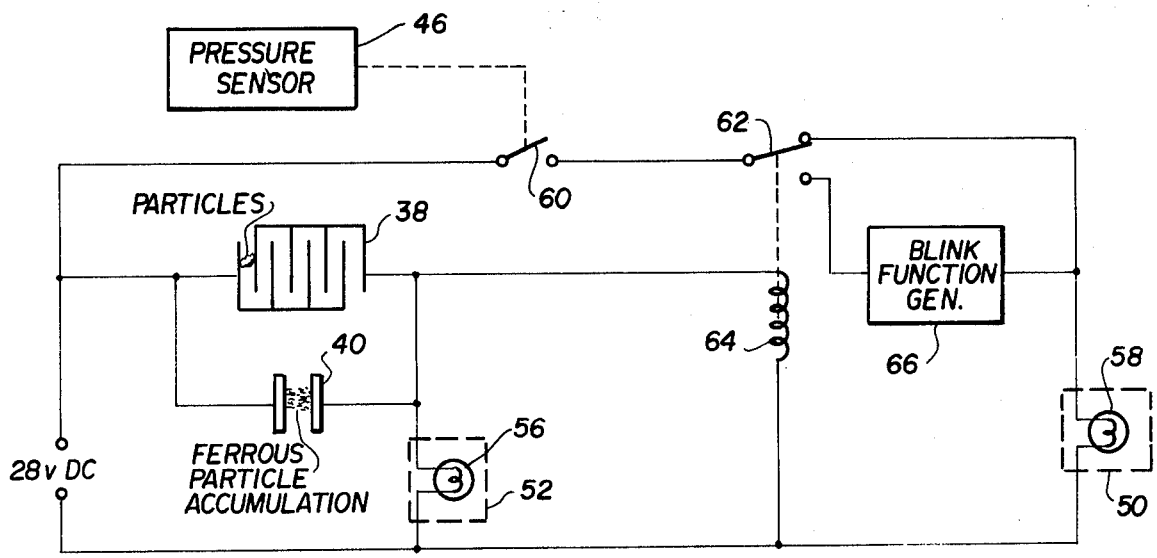
FIG. 4 which is a circuit diagram schematically illustrating the various components of the debris detection apparatus of the invention.

The purpose for the various indications can be better understood by references to FIG. 4. FIG. 4 illustrates a circuit including: the screen 38; the magnetic chip detector 40; the cockpit display panel 50 including light indicator 58; the differential pressure gauge contact 60; a switch 62 and control coil 64; a blink function generator 66; and the maintenance panel 52, including light indicator 56. The circuit of FIG. 4 is connected to a DC source, such as 28 VDC, and has three modes of operation: mode (1), a particle or particles impinge on screen 38 and/or sufficient ferrous particles accumulate on the magnetic chip detector 40, a circuit is completed to the light indicator 56 and an indication is rendered on the maintenance panel 52; mode (2), a sufficient pressure drop occurs across the filter 44 that contact 60 is closed and a circuit is completed to the light indicator 58 and an indication is rendered in the cockpit; mode (3), indicator 46 causes contact 60 to close; if either or both of indicators 38 and 40 are activated the coil 64 is energized throwing switch 62 to its opposite position (in dashed lines) causing thereby a pulsing of light indicator 58.

A pulsing of light indicator 58 signifies that a dangerous condition is developing in the system being served (transmission, for example), and that therefore appropriate action should be taken with respect to the system being served. For example, if the system being served is a helicopter transmission, the transmission should be shut down and inspected. A pulsing of light indicator 58 therefore represents a significant warning.

Since the indication giving by the differential pressure gauge 46 is significant, it is displayed in the cockpit. Since the indications given by the screen 38 and the detector 40 may not be as significant, i.e., a dangerous condition is not rapidly developing, they are only displayed in the maintenance panel 52. During routine maintenance, the panel 52 can be checked and if either the screen 38 or the detector 40 have been active, an appropriate indication will be visible (for example, the light 56, or even a mechanical indicator) then a manual check can be performed. The unit including the screen 38 and the detector 40 can be easily removed for inspection, without the need to interrupt the primary lubricating system.

Figure 5:
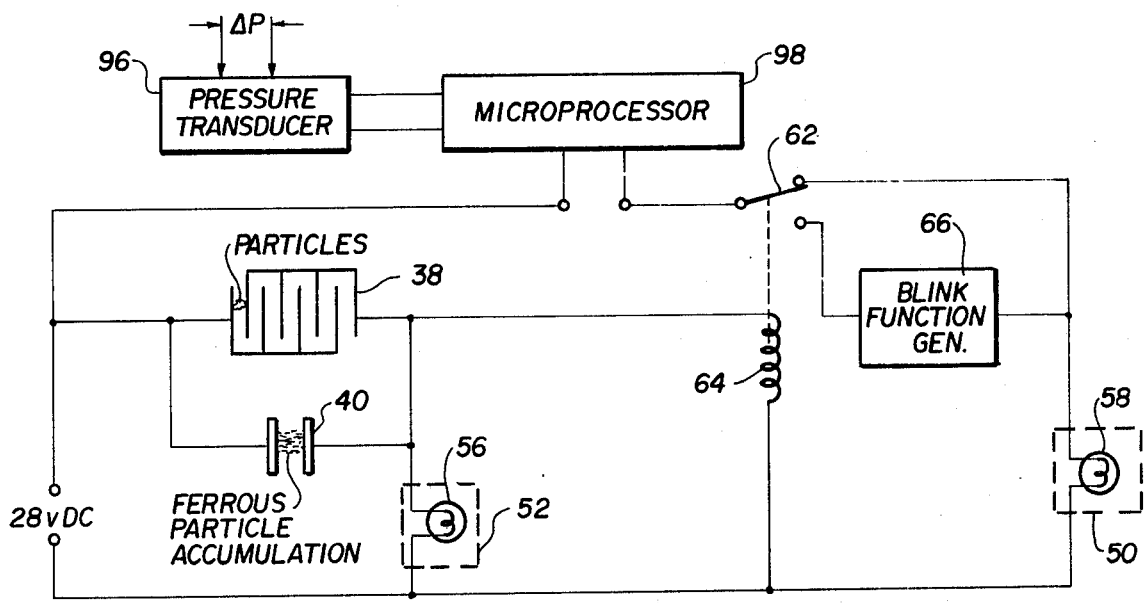
FIG. 5 which illustrates a variant of the circuit of FIG. 4.

When the pulsing of light indicator 58 is combined with a rate of debris accumulation indication at the filter 44, a dangerous condition exists in the system being served and immediate action is required. The rate of debris accumulation indication can be accomplished in several ways. It could be accomplished by manual inspection of the filter 44 prior to activating the fluid system. For example, if the system being served is a helicopter transmission, the filter 44 can be visually inspected before commencing the mission. If, for example, the filter 44 is clean at inspection, and a pulsing of the light indicator 58 occurs during flight, the pilot is on notice that the rate of debris accumulation is such that the mission should be aborted. Another means of indicating the rate of debris accumulation would be by utilizing the timing apparatus disclosed in U.S. Pat. No. 3,686,926. Still another means of indicating the rate of debris accumulation would be by the alternate embodiment of FIG. 4, i.e., the embodiment of FIG. 5. In FIG. 5, the differential pressure gauge 46 and its contact 60 are replaced by a pressure transducer 96 and a microprocessor 98 connected as shown. The pressure transducer 96 feeds pressure data detected across the filter 44 and feeds this pressure data to the microprocessor 98 which checks the rate of pressure change. When an acceptable rate of change is exceeded a circuit is closed through the switch 62 resulting in pulsing of the light indicator 58.

In the alternate embodiment illustrated in FIG. 2 the reservoir 68 is a modification of the reservoir 10. Within the reservoir 68 downwardly sloping surfaces 70 and 72 are situated. These surfaces serve a purpose similar to that of surfaces 14 and 16. The surfaces 70 and 72 converge at an opening 74 to which a perforeated sheet or screen 76 is connected. A secondary fluid reservoir or sump 80 is provided concentric with the screen 76. The sump 80 includes an upper wall defining a downwardly directed flange 82, and downwardly sloping surfaces 84 and 86.

In operation the lubricant drains through the opening 74 and develops a pool 88 within the sump 80. It then overflows the sump 80 forming the pool 90 which serves as a source of lubricating fluid for the primary flow. Debris, both colloidal and otherwise, are carried through the opening 74 into the sump 80. Within the sump 80 the surfaces 84 and 86 direct the heavy debris to the opening 18. The colloidal debris is carried with the fluid through the opening 18. The colloidal debris is also carried with the fluid as it spills over to form the pool 90. This debris is passed through the screen 30 and collected at the filter 42. The flange 82 ensures that the larger and heavier debris is not carried with the spill over fluid into the pool 90. Since the pool 90 is relatively free of any large debris, the screen 30 need not have the cap and skirt as does the screen 30 of the embodiment of FIG. 1. With the exception noted, the system operates in a manner similar to that of the embodiment of FIG. 1.

In the alternate embodiment illustrated in FIG. 3, the modification lies in the delivery of the lubricating fluid to the reservoir 68. FIG. 3 illustrates a so-called dry sump, i.e., one which is removed from the system being served. Lubricating fluid is drawn by a pump 92 through a line 94 and delivered to the reservoir 68. The screen 38 and magnetic chip detector 40 are located immediately upstream of the pump 92. While this location is preferred, it can also be located as shown in FIG. 2 but this would require a protecting screen ahead of pump 92. The location of FIG. 3 in this type of system is preferred since inspection would not require reservoir draining or the use of self-closing devices. With the exceptions noted, the embodiment of FIG. 3 operates in a manner similar to that of FIGS. 1 and 2.

The screen 38 has openings dimensioned within the range 0.10 inches×0.10 inches to 0.03 inches×0.03 inches. The fine mesh screen filters 42 and 44 can have an opening size of 0.03 inches×0.03 inches to 15 microns.

The microprocessor 98 can be any 8 bit processor, such as, for example, the Intel 8085 or the Motorola 6502.

With the present invention delivery of all accessible debris to one area, the secondary flow inlet, is accomplished. This is accomplished by funneling the generated debris to the secondary flow inlet. Contoured sumps sloping to a single collection point can be used. Also, funnel-like baffles can be used. All but colloidal debris is shielded from the primary flow and a single easily removable unit is provided in the secondary flow for capturing both small and larger sized debris. Also a screen/filter unit functions with a pressure differential switch downstream of the secondary flow pump to provide significant warning of impending failure.

The system of the invention is designed to provide a high degree of flexibility and simplicity in detecting and monitoring failure debris in an oil circulating system. For example, in the transmission of a helicopter, pilot warning is given for only significant conditions. Thus, pilots are relieved from monitoring incipient failure conditions and abortive flights for such conditions are avoided. On the other hand, pilot confidence and safety is enhanced by providing pilot warning for those rare conditions of deterioration which produce failure debris at a rapid rate.

We claim:

1. In a fluid system having a reservoir from which a primary flow and a secondary flow originate for serving a common system, a system for detecting debris originating in the common system being served, comprising:

means for diverting debris from the common system being served to the secondary flow at its point of origin in the reservoir;

monitoring means located in said secondary flow for detecting debris accumulation within the secondary flow.

2. The system for detecting debris as defined in claim 1, wherein the means for diverting debris includes the bottom wall of the reservoir, said wall defining a downwardly sloping surface portion to the point of origin of the secondary flow.

3. The system for detecting debris as defined in claim 2, wherein the bottom wall of the reservoir slopes downwardly in the form of a cone to the point of origin of the secondary flow, said point of origin being located at the apex of said cone.

4. The system for detecting debris as defined in claim 2, wherein the means for diverting debris further includes shielding means for shielding the point of origin of the primary flow, thereby excluding debris from entering the primary flow.

5. The system for detecting debris as defined in claim 1, wherein the flow capacity of the primary flow is greater than the flow capacity of the secondary flow.

6. The system for detecting debris as defined in claim 1, further comprising:
a pump for generating the secondary flow.

7. The system for detecting debris as defined in claim 6, wherein the monitoring means includes a filter and a differential pressure sensor both located downstream of the pump, for detecting the amount of debris accumulated.

8. The system for detectng debris as defined in claim 7, wherein the monitoring means further includes a screen located upstream of the pump and at the point of origin of the secondary flow for detecting the presence of metallic debris of at least a predetermined size.

9. The system for detecting debris as defined in claim 8, wherein the monitoring means further includes a magnetic chip detector located at the point of origin of the secondary flow, for detecting the presence of ferrous debris.

10. The system for detecting debris as defined in claim 1, wherein the means for diverting debris includes a downwardly sloping surface within the reservoir defining an opening and a perforated screen which extends from the opening in the downwardly sloping surface toward the point of origin of the secondary flow.

11. The system for detecting debris as defined in claim 10, wherein the means for diverting further includes a secondary flow container located within the reservoir and concentric with the perforated screen, the volume of said secondary flow container being less than that of the reservoir.

12. The system for detecting debris as defined in claim 11, wherein the secondary flow container includes an inwardly directed flange about its upper periphery which serves to retain debris within the secondary flow container.

13. The system for detecting debris as defined in claim 1, further comprising:
display means connected to said monitoring means for providing a visual display indicative of the debris accumulation.

14. In a lubricating system having a reservoir from which a primary flow and a secondary flow originate, said secondary flow serving as an auxilliary source of lubrication in the event of failure of the primary flow, a system for detecting debris, comprising:

means for diverting debris to the secondary flow at its point of origin in the reservoir;
means for shielding the point of origin of the primary flow, thereby excluding debris from entering the primary flow; and
monitoring means located in said secondary flow for detecting debris accumulation within the secondary flow.

15. The system for detecting debris as defined in claim 14, wherein the flow capacity of the primary flow is greater than the flow capacity of the secondary flow.

16. The system for detecting debris as defined in claim 14, further comprising:
a pump for generating the secondary flow, and wherein the monitoring means includes: a filter and a differential pressure sensor both located downstream of the pump for detecting the amount of debris accumulated; a filter located upstream of the pump and at the point of origin of the secondary flow for detecting the presence of metallic of at least a predetermined size, and a magnetic chip detector located at the point of origin of the secondary flow for detecting the presence of ferrous debris.

17. The system for detecting debris as defined in claim 16, wherein the means for diverting debris includes the bottom wall of the reservoir, said wall defining a downwardly sloping surface portion to the point of origin of the secondary flow.

18. The system for detecting debris as defined in claim 17, wherein the bottom wall of the reservoir slopes downwardly in the form of a cone to the point of origin of the secondary flow, said point of origin being located at the apex of said cone.

19. The system for detecting debris as defined in claim 16, wherein the means for diverting debris includes a downwardly sloping surface within the reservoir defining an opening, a perforated screen which extends from the opening in the downwardly sloping surface toward the point of origin of the secondary flow, and a secondary flow container located within the reservoir and concentric with the perforated screen, the volume of said secondary flow container being less than that of the reservoir.

20. The system for detecting debris as defined in claim 19, wherein the secondary flow container includes an inwardly directed flange about its upper periphery which serves to retain debris within the secondary flow container.

21. The system for detecting debris as defined in claim 20, further comprising:
display means connected to said monitoring means for providing a visual display indicative of the debris accumulation.

22. A method for detecting debris within a fluid system, said system having a reservoir from which a primary flow and a secondary flow originate, the method comprising the steps of:
diverting debris to the secondary flow at its point of origin in the reservoir;
shielding the point of origin of the primary flow, thereby excluding debris from entering the primary flow; and
detecting the debris accumulation within the secondary flow.

23. The method for detecting debris as defined in claim 22, wherein the rate of debris accumulation within the secondary flow is detected.

* * * * *